United States Patent
Zulkarnaini et al.

(10) Patent No.: US 9,358,260 B2
(45) Date of Patent: Jun. 7, 2016

(54) OPTIMIZED EXTRACTION PROCESS FOR OBTAINING LABISIA PUMILA EXTRACT

(71) Applicant: Pharmaniaga Bhd, Shah Alam (MY)

(72) Inventors: Defri bin Zulkarnaini, Shah Alam (MY); Noridayu Che Ani, Shah Alam (MY); Miau Ching Ho, Shah Alam (MY); Visweswaran Navaratnam, Shah Alam (MY); Venkatesh Gantala, Shah Alam (MY)

(73) Assignee: PHARMANIAGA BHD, Shah Alam (MY)

( * ) Notice: Subject to any disclaimer, the term of this patent is extended or adjusted under 35 U.S.C. 154(b) by 517 days.

(21) Appl. No.: 13/759,473

(22) Filed: Feb. 5, 2013

(65) Prior Publication Data

US 2013/0209594 A1 Aug. 15, 2013

(30) Foreign Application Priority Data

Feb. 10, 2012 (MY) .......................... PI 2012700020

(51) Int. Cl.
*A61K 36/185* (2006.01)

(52) U.S. Cl.
CPC ........... *A61K 36/185* (2013.01); *A61K 2236/39* (2013.01)

(58) Field of Classification Search
CPC ...................................................... A61K 36/18
USPC .................................................. 424/773, 774
See application file for complete search history.

(56) References Cited

U.S. PATENT DOCUMENTS 7,879,368 B2 * 2/2011 Yusoff et al. .................. 424/725
2010/0303933 A1 12/2010 Qazi et al.

* cited by examiner

*Primary Examiner* — Chris R Tate
*Assistant Examiner* — Deborah Davis
(74) *Attorney, Agent, or Firm* — Merchant & Gould P.C.

(57) ABSTRACT

The present invention relates to a process for obtaining a *Labisia pumila* water extract comprising the steps of: obtaining an extract from dried *Labisia pumila* plant material using water extraction, filtering the extract to obtain filtrate and *Labisia pumila* plant material residue, re-extracting the *Labisia pumila* residue using water extraction, centrifuging the *Labisia pumila* extracts to obtain a supernatant, characterized in that, the *Labisia pumila* plant material includes leaves and roots in a ratio of 3:2 by weight and ratio of the dried plant material to water used in the water extraction process is 1:10 by weight, wherein the yield obtained from initial extraction is 7% to 8% and the extra yield obtained from re-extraction is 33% to 38% and the total yield obtained from the extraction is 10% to 12%.

7 Claims, 1 Drawing Sheet

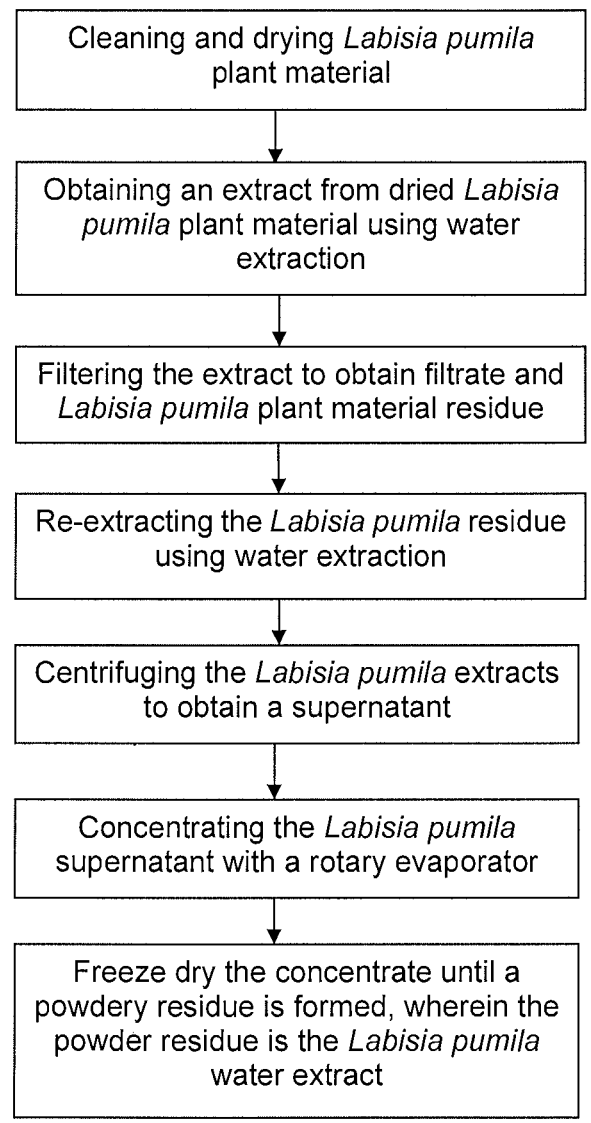

OPTIMIZED EXTRACTION PROCESS FOR OBTAINING LABISIA PUMILA EXTRACT

CROSS-REFERENCE TO RELATED APPLICATIONS

This application claims benefit of Malaysian Serial No. PI 2012700020, filed Feb. 10, 2012 in Malaysia, which application is incorporated herein by reference in its entirety.

BACKGROUND OF THE INVENTION

1. Field of the Invention

This invention relates to an optimized extraction process for obtaining Labisia pumila extract in powdery form through water extraction process and freeze drying.

2. Description of Related Arts

Labisia pumila, or known as Kacip Fatimah in Malay language, is a wild plant that can be found widely in the shade of tropical forest floors. It is famous as herbal medicine and has been used for centuries to enhance vitality, improve blood circulation and firm and tone muscles after childbirth. Kacip Fatimah is also sought for a variety of health benefits, including relieving fatigue and promoting hormonal balance and emotional well-being.

By viewing valuable pharmacological application of Labisia pumila, a number of researches have been made to focus on the preparation of Labisia pumila. Various extraction methods have been utilised in order to obtain the essence of the Labisia pumila including water extraction method. Extract from the Labisia pumila are usually obtained in powdery form and is made into capsules and tablets for consumption. Therefore, the raw material sources and extraction process of Labisia pumila are crucial in assuring quality of the extract.

Preparations from the same type of plant may vary in their chemical profile, depending on extraction procedures and raw material sources. For this reason, assessing the qualitative and quantitative of herbal products presents a greater challenge in herbal industry. The purity and high yield of an extract rely on the parameters and conditions of the extraction process. Without a proper extraction process, the yield and quality of extracts obtained might be poor.

The concept of standardization is widely used to address standard criteria for consistency and quality control of specific herbal preparations. One example of method and parameter to prepare Labisia pumila standardized extract that has been disclosed in prior art is briefly summarized and distinguished over the present invention as below.

Malaysia Patent No. MY-20054784-P has disclosed a process for preparing water-soluble Labisia pumila extract, and to obtain a reproducible chemical profile by reverse-phase high performance liquid chromatography (RP-HPLC). The process for preparing Labisia pumila extract as mentioned in the said patent comprises the steps of extracting dried Labisia pumila material with water to form a water-soluble extract and drying the extract obtained. The ratio of dried Labisia pumila plant material to water is particularly selected at 1:6 and resulted 4-5% yield. One marker compound, which is a gallic acid, was isolated and identified by applying the cited method. Comparatively, the present invention introduces a method of extraction that is capable of producing higher yields. Furthermore, the present invention utilizes freeze drying method to obtain finer Labisia pumila extract powder form.

Malaysia Patent No. MY-2010002278-P disclosed another approach for preparing water-soluble Labisia pumila extract and the use of the extract in a pharmaceutical preparation. The patent disclosed a process for preparing Labisia pumila extract which comprises the steps of extracting dried Labisia pumila plant material with water to form a water-soluble extract and drying the extract obtained, characterized in that the extract having the capability to develop a composition for immunopotenting activity. In this method, only dried leaves of Labisia pumila in powder form was used for the extraction and the extraction of plant with water is particularly in ratio of 1:8.

Accordingly, it can be seen from the prior art that there is a need to provide an optimized extraction process of Labisia pumila plants that will give higher yield and quality of the Labisia pumila extract.

SUMMARY OF INVENTION

It is an objective of the present invention to provide a process for obtaining a Labisia pumila extract with higher yield.

It is also an objective of the present invention to provide a process for obtaining a Labisia pumila extract using leaves and roots of Labisia pumila in a ratio of 3:2.

It is yet another objective of the present invention to provide a process for obtaining a Labisia pumila extract by water extraction process with a 1:10 ratio of plant material over distilled water or reverse osmosis water or deionised water.

It is a further objective of the present invention to provide a process for obtaining a Labisia pumila extract in powdery form by freeze-drying.

Accordingly, these objectives may be achieved by following the description of the present invention. The present invention relates to a process for obtaining a Labisia pumila extract comprises the steps of: obtaining an extract from dried Labisia pumila plant material using water extraction, filtering the extract to obtain filtrate and Labisia pumila plant material residue, re-extracting the Labisia pumila residue using water extraction, centrifuging the Labisia pumila extracts to obtain a supernatant, characterized in that the Labisia pumila plant material includes leaves and roots in a ratio of 3:2 by weight and ratio of the dried plant material to water used in the water extraction process is 1:10 by weight.

BRIEF DESCRIPTION OF THE DRAWINGS

The features of the invention will be more readily understood and appreciated from the following detailed description when read in conjunction with the accompanying drawings of the preferred embodiment of the present invention, in which:

FIG. 1 is a flow chart of a process for obtaining a Labisia pumila extract according to the preferred embodiment of present invention;

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting but merely as a basis for claims. It should be understood that the drawings and detailed description thereto are not intended to limit the invention to the particular form disclosed, but on the contrary, the invention is to cover all modification, equivalents and alternatives falling within the scope of the present invention as defined by the appended claims. As used throughout this application, the word "may" is used in a permissive sense (i.e., meaning having the potential to), rather than the mandatory sense (i.e., meaning must). Similarly, the words "include," "including," and "includes" mean including, but not limited to. Further, the words "a" or "an" mean "at least one" and the word "plurality" means one or more, unless otherwise mentioned. Where the abbreviations or technical terms are used, these indicate the commonly accepted meanings as known in the technical field. For ease of reference, common reference numerals will be used throughout the figures when referring to the same or similar features common to the figures. The present invention will now be described with reference to FIG. 1.

The present invention relates to a process for obtaining a *Labisia pumila* extract comprising the steps of obtaining an extract from dried *Labisia pumila* plant material using water extraction, filtering the extract to obtain filtrate and Labisia pumila plant material residue, re-extracting the *Labisia pumila* residue using water extraction, centrifuging the *Labisia pumila* extracts to obtain a supernatant, characterized in that the *Labisia pumila* plant material includes leaves and roots in a ratio of 3:2 by weight and ratio of the dried plant material to water used in the water extraction process is 1:10 by weight.

Prior to the extraction process, the plant material which includes leaves and roots of the *Labisia pumila* is cleaned to remove any impurities on the plant material.

Thereafter, the *Labisia pumila* plant materials are oven dried for three days at temperature of 40° C. to a constant weight to dehydrate the plant material. The drying step can be conducted using various methods including oven dryer. The dried plant material which comprises dried leaves and dried roots of the *Labisia pumila* is weighed in a ratio of 3 parts of leaves and 2 parts of roots.

In a preferred embodiment of the process for obtaining a *Labisia pumila* extract, the dried *Labisia pumila* plant material is cut into smaller pieces to facilitate the extraction process.

In a preferred embodiment of the process for obtaining a *Labisia pumila* extract, the dried *Labisia pumila* plant material is extracted through water extraction using distilled water or reverse osmosis water or deionised water, wherein the water is used as a solvent during the extraction process to produce higher quality of extract. The quantity ratio of dried plant material to the solvent is preferably one part of dried plant material to ten parts of solvent.

In a preferred embodiment of the process for obtaining a *Labisia pumila* extract, the water extraction is performed at a temperature of 80° C. for three hours with stirring to obtain uniform extract.

In the next step, the extract is filtered to obtain filtrate and *Labisia pumila* plant material residue.

The *Labisia pumila* residue is re-extracted using water extraction. In a preferred embodiment, the residue is re-extracted with the same volume of water used in the initial extraction and re-extracted at a temperature of 80° C. for an hour with stirring. The *Labisia pumila* extracts is then centrifuged to obtain the supernatant. In a preferred embodiment of the process for obtaining a *Labisia pumila* extract, the centrifuging is conducted at 3500 rpm for 15 minutes.

In a preferred embodiment of the process for obtaining a *Labisia pumila* extract, the supernatant is further filtered and concentrated using rotary evaporator at temperature of 75° C. to evaporate the excessive solvent from the supernatant. The supernatant is filtered using Buchner Funnel.

In a preferred embodiment of the process for obtaining a *Labisia pumila* extract, the supernatant is freeze-dried to obtain powdery residue. The supernatant is transferred into a freeze dryer vessel and frozen in a freezer at −20° C. The frozen extract is then dried in a freeze dryer until a powdery residue is obtained.

In a preferred embodiment of the present invention, the yield obtained from initial extraction is 7% to 8%. The re-extraction of the *Labisia pumila* residue provides 33% to 38% extra yield and the total yield obtained from the extraction is 10% to 12%.

FIG. 1 shows the flow of the process for obtaining a *Labisia pumila* extract in accordance to the preferred embodiment of the present invention.

Although the present invention has been described with reference to specific embodiments, also shown in the appended figure, it will be apparent for those skilled in the art that many variations and modifications can be done within the scope of the invention as described in the specification and defined in the following claims.

We claim:

1. A process for obtaining a *Labisia pumila* extract product comprising the steps of:
    extracting dried *Labisia pumila* plant material with water at ratio of 1:10, respectively, to obtain a first aqueous extract;
    filtering the first aqueous extract to obtain a filtrate and a plant residue;
    re-extracting the plant residue with water to obtain a second water extract; and
    centrifuging the first and second water extracts to obtain a supernatant, wherein the supernatant is the *Labisia pumila* extract product, and wherein the dried *Labisia pumila* plant material comprises leaves and roots in a ratio of 3:2 by weight.

2. The process according to claim 1, wherein the water used to obtain the first and/or second aqueous extract is distilled water or reverse osmosis water or deionised water.

3. The process according to claim 1, wherein the initial water extraction is performed at temperature of 80° C. for 3 hours with stirring.

4. The process according to claim 1, wherein the re-extracting is performed at temperature of 80° C. for an hour.

5. The process according to claim 1, wherein the centrifuging is conducted at 3500 rpm for 15 minutes.

6. The process according to claim 1, wherein the supernatant is further filtered and concentrated using rotary evaporator at temperature of 75° C.

7. The process according to claim 1, wherein the supernatant is further freeze-dried to obtain a powdery residue.

\* \* \* \* \*